United States Patent [19]

Eckstein et al.

[11] Patent Number: 4,880,782

[45] Date of Patent: Nov. 14, 1989

[54] METHOD OF TREATING VIRAL INFECTIONS IN HUMANS AND COMPOSITIONS THEREFOR

[75] Inventors: Fritz Eckstein; Gerhard Hunsmann; Heinz Hartmann, all of Göttingen, Fed. Rep. of Germany

[73] Assignees: Max-Planck-Gesellschaft zur Foederung der Wissenschaften e.V.; Deutsches Primatenzentrum GmbH, both of Goettingen, Fed. Rep. of Germany

[21] Appl. No.: 41,147

[22] Filed: Apr. 22, 1987

[30] Foreign Application Priority Data

Nov. 21, 1986 [DE] Fed. Rep. of Germany ....... 3639780
Mar. 18, 1987 [DE] Fed. Rep. of Germany ....... 3708849

[51] Int. Cl.$^4$ .................... A61K 31/70; C07H 19/07
[52] U.S. Cl. ........................................ 514/45; 514/46; 514/49; 514/50; 514/885; 536/23; 536/24; 536/26
[58] Field of Search .......... 514/45, 46, 49, 50; 536/23, 24, 26

[56] References Cited

U.S. PATENT DOCUMENTS

3,775,397  11/1973  Etzold et al. .................... 536/23
4,724,232   2/1988  Rideout et al. .................. 514/50

FOREIGN PATENT DOCUMENTS

0002192  6/1972  European Pat. Off. ............. 514/45
196185  10/1986  European Pat. Off.
199451  10/1986  European Pat. Off.
217580   4/1987  European Pat. Off.
0961354  8/1985  U.S.S.R. ........................ 536/26
1053474  8/1985  U.S.S.R. ........................ 536/24

OTHER PUBLICATIONS

Cheng et al., The Chemical Abstracts, 106:152055s, (1987).
De Clercq et al., Biochemical Pharmacology, 29, pp. 1849-1851, (1980).
Lin et al., The Chemical Abstracts, 98:119272d, (1983).
Robins, "Synthetic Antiviral Agent", C & EN, Jan. 1986.
Herdewijn et al., J. Med. Chem., 30, 1270-1278, (1987).
Mitsuya et al., Proc. Natl. Aca. Sci., U.S.A., vol. 83, pp. 1911-1915, Mar. 1986.
Cheng et al., The J. of Biological Chemistry, vol. 262, No. 5, pp. 2187-2189, (1987).
Chen et al., Biochemical Pharmacology, vol. 36, No. 24, pp. 4361-4362, (1987).
Chem. Abst., 105(19):165001a, (11/10/86).
Biomed. Biochem. Acta, 44(10): K63-73, (1985).
Biochem. Biophys. Res. Comm., 148(1): 78-85, (10/14/87).
J. Biol. Chem., 262(5): 2187-89, (2/87).
J. Med. Chem., 30(8): 1270-78, (Aug. 1987).
Biochem. & Biophys. Res. Comm., 145(3): 1080-6, (6-30-87).
Biochem. Pharm., 29(12): 1849-51, (1980).

*Primary Examiner*—John W. Rollins
*Attorney, Agent, or Firm*—Felfe & Lynch

[57] ABSTRACT

A method of treating viral diseases in a human subject is disclosed. The method involves applying effective amounts of the compound:

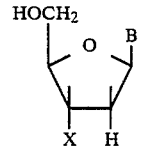

wherein X is an azido group, a methoxy radical or a fluorine atom and B is thymine, uracil, guanine, cytosine, purine or hypoxanthine if X is methoxy or fluorine, and B is guanine, purine or hypoxanthine if X is azido or a pharmaceutically acceptable salt thereof. Also disclosed are compositions and compounds useful in the method.

12 Claims, 5 Drawing Sheets

METHOD OF TREATING VIRAL INFECTIONS IN HUMANS AND COMPOSITIONS THEREFOR

FIELD OF THE INVENTION

This invention relates to a method of treating humans with diseases brought about by viruses which are characterized by RNA-dependent DNA polymerase. Of special interest are methods of treating retrovirus infections, especially those caused by Human Immunodeficiency Virus (HIV), which is the cause of Acquired Immune Deficiency Syndrome (AIDS).

BACKGROUND AND PRIOR ART

Patients exhibiting acquired immune deficiency syndrome (AIDS) were first observed in 1981. While occurrences were at first isolated and appeared to be confined to the male homosexual population, this observation very quickly proved to be wrong as AIDS was found to be widespread across all population groups.

AIDS infection has been characterized as an epidemic in some parts of the world, and it is expected that other parts of the world will soon characterize the infection as such.

In U.S. Pat. No. 4,520,113, filed Apr. 23, 1984, Gallo et al. stated that the evidence suggested that "the disease spreads by the transmission of an infectious agent. The primary targets of affliction in the human body are specific subpopulations of T-cells. The severe immune deficiency of these patients results from an unusually low proposition of helper T-cells (T4) in their lymphocyte population, thus reducing the availability of many T4 helper functions, among which is the production of antibodies by B-cells".

Gallo, et. al., *Science* 220:865-867 (May 20, 1983) proposed that the causative agent of AIDS is a human T-cell leukemia virus (HTLV). These viruses are characterized by pronounced tropism for T4 cells, reverse transcriptase with high molecular weight (100 kd), and with preference for $Mg^{2+}$ for optimal enzymatic activity. Schüpbach, et al., Science 224:503-505 (May 4, 1984). The work of Barre-Sinussi, et al., *Science* 220:868-871 (May 20, 1983), agreed with the *Gallo* hypothesis, and differed only in its calling the virus lymphadenopathy AIDS associated virus (LAV). Currently, most scientists in the field refer to the virus as human immunodeficiency virus (HIV), and this term will be used hereafter.

Investigations began almost immediately for suitable methods and materials to treat HIV infections, which are always fatal. It must be pointed out that investigations proceeded on several levels. The first of these is on the "prevention" level, i.e., attempts to prevent infection from occurring. This approach involves modifying behavior patterns, and is not discussed further herein. The second approach has been investigations along the lines of developing an immune response to the virus, by way of a vaccine. Research has been slow in this area, for several reasons. HIV infections occur only in humans, and are always fatal. Vaccine research generally involves introducing an etiolated or dead strain of the virus to the subject in order to develop an immune response. Animal models do not work, and the risks involved in human trials have been too great to advance work in this field very far.

Yet a third approach has been to treat the "follow-up" infections, such as *Pseudomonas carinii* pneumonia (PCP), which develop after HIV devastates the immune system. Sulfamethoxazole, sold as "Bactrim" has been one effective drug. It is extremely toxic, however, and many AIDs patience have allergies to it. These factors result in limited usefulness for the drug. Where sulfamethoxazole cannot be used, pentamidine isethionate, known as an anti-protozoan, is used. This drug has proven to be somewhat more effective when administered to AIDs patients in intravenous or aerosol form, but it too is extremely toxic and has various known and suspected side effects. Long term therapy with either of these substances is not possible.

The fourth and final approach to treating HIV is via drugs which interfere with the virus' ability to replicate. This area has received much attention because, ultimately, it is the only approach which will destroy or limit the infection at its source.

The current drug of choice in this area is azidothymidine, also referred to as AZT. AZT, in severely limited trials, has been shown to interfere with viral replication, which results in some remission of the infection.

There have, however, been problems with AZT as well. It is toxic, and is suspected of suppressing bone marrow function. See, e.g. Kolata, *Science* 225:1463 (Mar. 20, 1987). The regime which is used for treatment with AZT requires very stringent conditions which must be followed by the patient for the drug to be effective. In view of this, as well as AZT's toxicity, research did not and has not stopped following the positive results obtained with the drug.

It is therefore an object to the invention to provide a method of treating humans infected with viruses characterized by RNA-dependent polymerases, especially those humans infected with human immuno-deficiency virus (HIV).

It is a further object of the invention to provide a composition useful in treating individuals infected with human immunodeficiency viruses.

How these as well as other objects of the invention are achieved will be made explicit by the disclosure which follows.

SUMMARY OF THE INVENTION

A method of treating humans infected with viruses characterized by RNA dependent polymerases, comprising administering to an infected individual an effective amount of at least one compound of the formula wherein X is an azido group, a methoxy radical or a fluorine atom. B is thymine, uracil, guanine, cytosine, hypoxanthine, or purine if X is a methoxy radical or a fluorine atom and B is a guanine, purine or hypoxanthine radical if X is azido, as well as pharmaceutically acceptable salts thereof. Compositions are also prepared which comprise at least one compound as described supra, taken with conventional pharmaceutical carriers and diluents.

DETAILED DESCRIPTION OF PREFERRED EMBODIMENTS

The active materials described supra will be seen to be 9-(beta-D-deoxyribofuranosyl) nucleosides of the thymidine uridine guanosine cytidine purinnucleoside or inosine series. Of particular interest are the specific compounds 3'-azido-2',3'-dideoxy guanosine, 3'-azido-2',2'-dideoxyinosine, 3'-fluoro,2',3'-dideoxy guanosine and 3'-fluoro-3'-deoxythymidine. Th first compound is prepared according to the process described in Imazawa, et. al., J. Org. Chem. 43:3044–3048 (1978), the disclosure of which is incorporated by reference herein.

It is surprising that the compounds used according to the invention are active against HIV because, from Clerco,,'et. al., *Biochem. Pharm.* 29: 1849–1851 (1980), one is taught that 3'-azido-2',-3'-dideoxyguanosine shows no measurable antiviral activity against vaccinia virus, herpes simplex virus 1, or vesicular stomatitis virus.

The preparation of 3'-azido-2',-3'-dideoxyguanosine takes place in principle, by transglycosylation of the corresponding 5'-0-acetyl- or 5'-0-trimethylsilyl-3'-azido-3'-deoxythymidine with silylated N2-palmitoyl-guanine in the presence of trimethylsilyl-trifluoromethanesulphonate as catalyst.

The corresponding hypoxanthine compound is obtained in an analogous manner by the use of the corresponding palmitoyl-hypoxanthine. Alternatively these guanine and hypoxanthine compounds may be obtained by the reaction of 1-0-methyl-5-0-(4-methylbenzoyl)-3-azido-2,3-dideoxy-D-ribofuranose, obtained according to the procedure of N. D. Dyatkina and A. V. Azhayev described in Synthesis, 1984, p. 961, with silylated guanine or hypoxanthine with the help of a catalyst, for example trimethylsilyl-trifluoromethanesulphonate, according to the procedure of H. Vorbruggen, K. Krokiewics and B. Benna, described in Chem. Ber. 114, p. 1234/1981. The corresponding guanine and hypoxanthine compounds with a fluorine atom or a methoxy residue in 3-position of the 2-deoxy-ribofuranosyl structure can be obtained from 3'-fluoro-3'-deoxy- or 3'-0-methyl-3-deoxythymidine by means of the same transglycosylation reaction. 2,3'-anhydro-1-(2-deoxy-β-D-xylofuranosyl)-thymine (briefly called $O^2$, $O^{3'}$-cyclothymidine), prepared according to G. Kowollik, K. Gärtner, P. Langen, *Tetrahedron Letters,* 1969, p. 3863, thereby again served as starting material. By reaction with sodium methylate the 3'-0-methyl-3'-deoxythymidine is prepared.

3'-fluoro-3'-deoxythymidine and its preparation is known from G. Etzold, R. Hintsche, G. Kowollik and P. Langen, Tetrahedron 27 (1971) pp. 2463-2472. The preparation is achieved in principle by the reaction of cyclothymidine in diethylene glycol with potassium hydrogen difluoride. The reaction products are separated on a kieselgel column with a mixture of $CHCl_3$ and methanol. A second purification step was done by chromatography on a LiChroprep RP-18 column with a mixture of 50 mM triethylammoniumcarbonate/5% acetonitrile.

3'-fluoro-3'-deoxythymidine can also be prepared by reacting the cyclothymidine, prepared by the method of G. Kowollik, G. Etzold, M. von Janta, Lipinski, K. Gärtner, B. Langen in J. Prakt. Chem. (1973) 315, p. 895, with hydrofluoric acid and aluminum trifluoride. Alternatively the cyclothymidine can be reacted with potassium fluoride in the presence the crown ether 18-crown-6 in dimethyl formamide or dioxane. Additionally the hypoxanthine compositions may be obtained from the corresponding adenine compositions, which are in part known from the literature cited above, by deamination with nitric acid or nitrosyl chloride.

The synthesis of 3'-fluoro-2',3'-dideoxyuridine is carried out in analogy to the preparation of 3'-fluoro-3'-deoxythymidine (G. Etzold, R. Hintsche, G. Kowollik and P. Langen, Tetrahedron 27 (1971) pp. 2463–2472). Thus the 2,3-anhydro-1-(2'-deoxy-β-D-xylofuranosyl-)-uracil (briefly called $O^2$, $O^{3'}$-cyclo-deoxy-uridine) is synthesized in analogy to $O^2$, $O^{3'}$-cycloethymidine (G. Kowollik, K. Gärtner and P. Lange, Tetrahedreon Letters (1969) p. 3863) starting with 2'-deoxyuridine. Cyclodeoxy-uridine is then reacted with potassium hydrogen difluoride in ethylene glycol to yield the 3,-fluoro-2',3'-deoxy-uridine. This composition served as starting material for the synthesis of 3'-fluoro-2',3'-deoxycytidine by an amination reaction according to B. F. L. Li, C. B. Reese and P. F. Swann (Biochem. 26 (1987) pp. 1986–1093) or W. L. Sung (J. Org. Chem. 47 (1982) pp. 3623–3628) by reaction with diphenyl phosphorchloridate or triisopropylbenzenesulphonylchloride or in another suitable activating reagent in the presence of nitrotriazole, triazole, or another convenient nucleophile, followed by reaction with ammonia.

The effectiveness of the active compounds used according to the present invention was ascertained in a biological system in which the HIV isolated from patients with AIDS and ARC was cultured with susceptable human T-cells. The in vitro pathogeneity of the so cultured HIV was determined with the use of $MT_4$-cells, a $T_4$-cell line for which HIV is cytopathic. The $MT_4$-cell line is described in Science, 229 (1985) pp. 563–566. The cytopathological effect was thereby monitored by measurement of the incorporation of thymidine into the cells. If the active materials according to the present invention, especially 3'-azido-2',3'-dideoxyguanosine was added to the $MT_4$-cells inocculated with HIV, then, even with nanomolar concentrations of the active materials it was possible to protect against the cytopathological effects brought about by the virus.

The toxicity determination also took place in the same system. In this case, $MT_4$-cells were exposed to the nucleoside analogue contained in the pharmaceutical composition according to the present invention as active materials in the absence of HIV and again the toxicity was determined on the basis of the incorporation of thymidine. From the so determined concentration for the achievement of an antiviral effect in comparison with the amount of active material necessary for a toxic effect, there was determined an in vitro therapeutic index.

For the most preferred 3'-azido-2',3'-dideoxyguanosine compound, this therapeutic index, in the case of the human cell line used, was equal or greater than $10^3$, for 3'-fluoro-3'-deoxythymidine greater than $10^3$, for 3'-fluoro2',3'-dideoxy-guanosine approximately 400. The experiments were carried out in such a manner, that samples of the supernatant of the cell line producing the virus were brought in stepwise dilution in microtiter plates which contained the $MT_4$-cell line. At the same moment radioactive labelled thymidine wa added to the microtiter plates and the incorporation of this substance, which runs parallel to the living activity of the cells, was measured. Under the influence of toxic concentrations of the active material according to the present invention or cytopathic amounts of virus-containing liquid, the incorporation of radioactively labelled thymidine decreased correspondingly.

Figure 1:
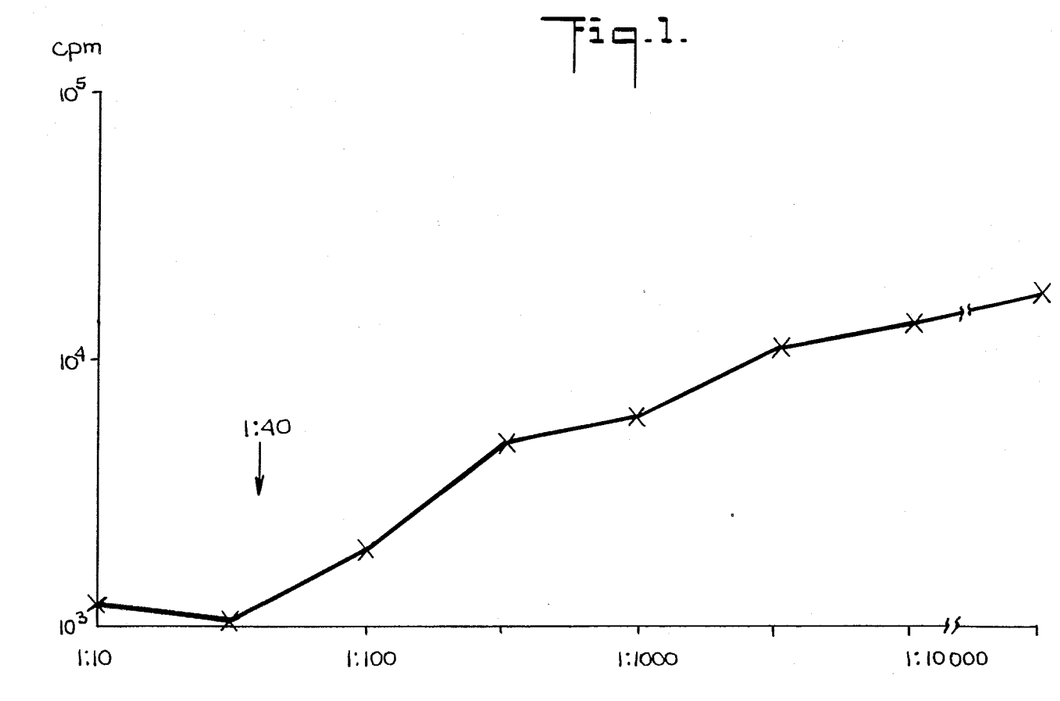
FIG. 1 shows graphically the pathogencity of HIV on $MT_4$ cells.

In FIG. 1 there is graphically illustrated the influence of different dilutions of the HIV virus-containing supernatant of the virus producing cell line (differing virus concentration) on the thymidine incorporation into $MT_4$-cells. The incorporation curve shows that up to a dilution of 1:30 the pathogeneity of HIV viruses leads to a very low thymidine uptake increase correspondingly and does achieve the highest value at a dilution of the virus-containing supernatant of 1:10000.

Figure 2:
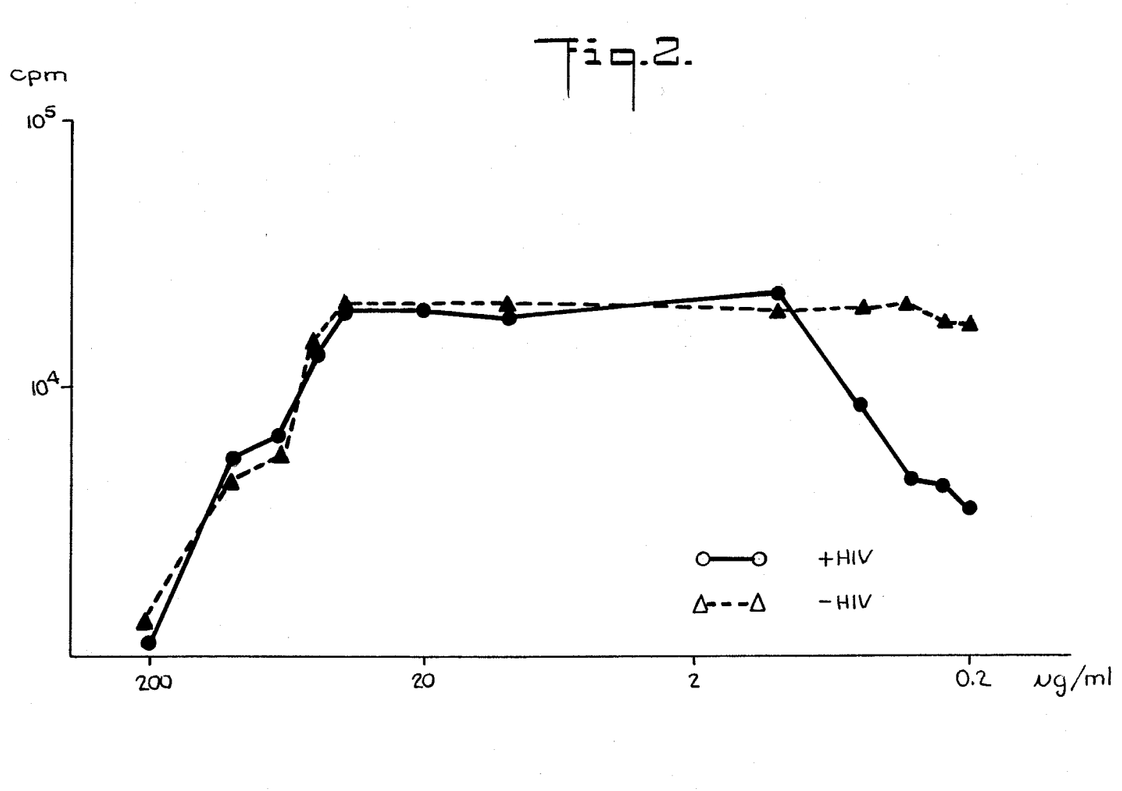
FIG. 2 shows results of in vitro viability studies when 3'-azido-2',3'-dideoxyguanosine was added to HIV infected cells.

Thus, FIG. 1 shows, in the case of a dilution of the cultured supernatant of 1:40, an almost maximum pathogeneity of the HIV on the $MT_4$-cells is still present. The investigations of the effectiveness of the active materials to the pharmaceutical compositions according to the present invention took place in the case of this virus dilution in that a premixed solution of virus dilution and of the active material to be investigated was added to the cell line sample and the thymidine incorporation again determined The results of these experiments with the preferred compound 3'-azido-2',3'-dideoxyguanosine are shown in FIG. 2 of the accompanying drawing. FIG. 2 shows graphically the relationship between the amount of active material added in $\mu g./ml.$ and the rate of thymidine incorporation in cpm (counts per minute). The curve indicated with −HIV was obtained in the absence of virus and the +HIV curve in the presence of virus. It shows that a concentration of 0.3 $\mu g./ml.$ of active material protects the cells with half maximum action against the pathogenic effect of a 1:40 dilution of the HIV parent liquid.

Figure 3:
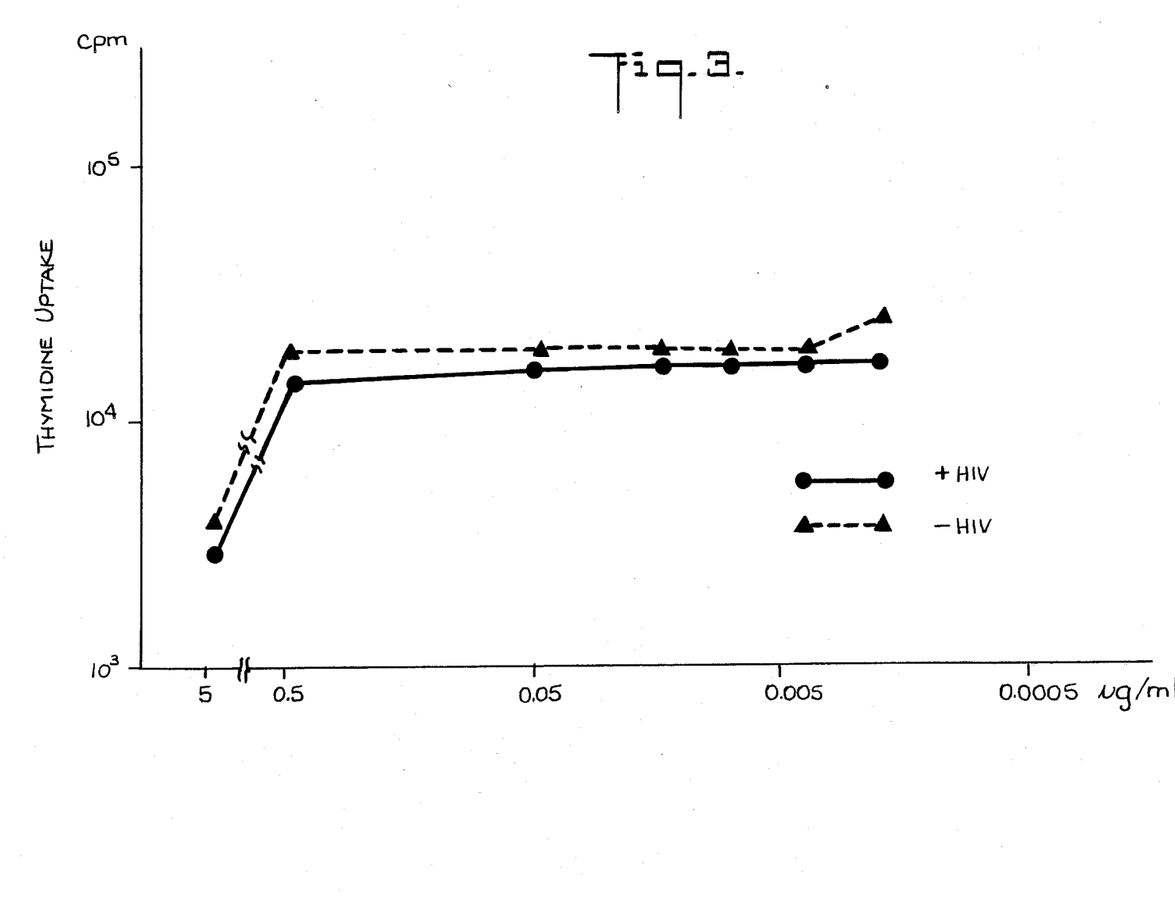
FIG. 3 shows results of in vitro viability studies when 3'-fluoro-3'-deoxythymidine was added to HIV infected cells.

FIG. 3 depicts the connection between the amount of 3'-fluoro-3'-deoxythymidine added in $\mu g./ml.$ and the thymidine incorporation in cpm (counts per minute) in analogy as explained for FIG. 2. It shows that at a concentration of less than 0.002 $\mu g./ml.$ the active compound protects the cells already with half maximal action against the pathogenic effect of a 1:40 dilution of the HIV parent liquid.

Figure 4:
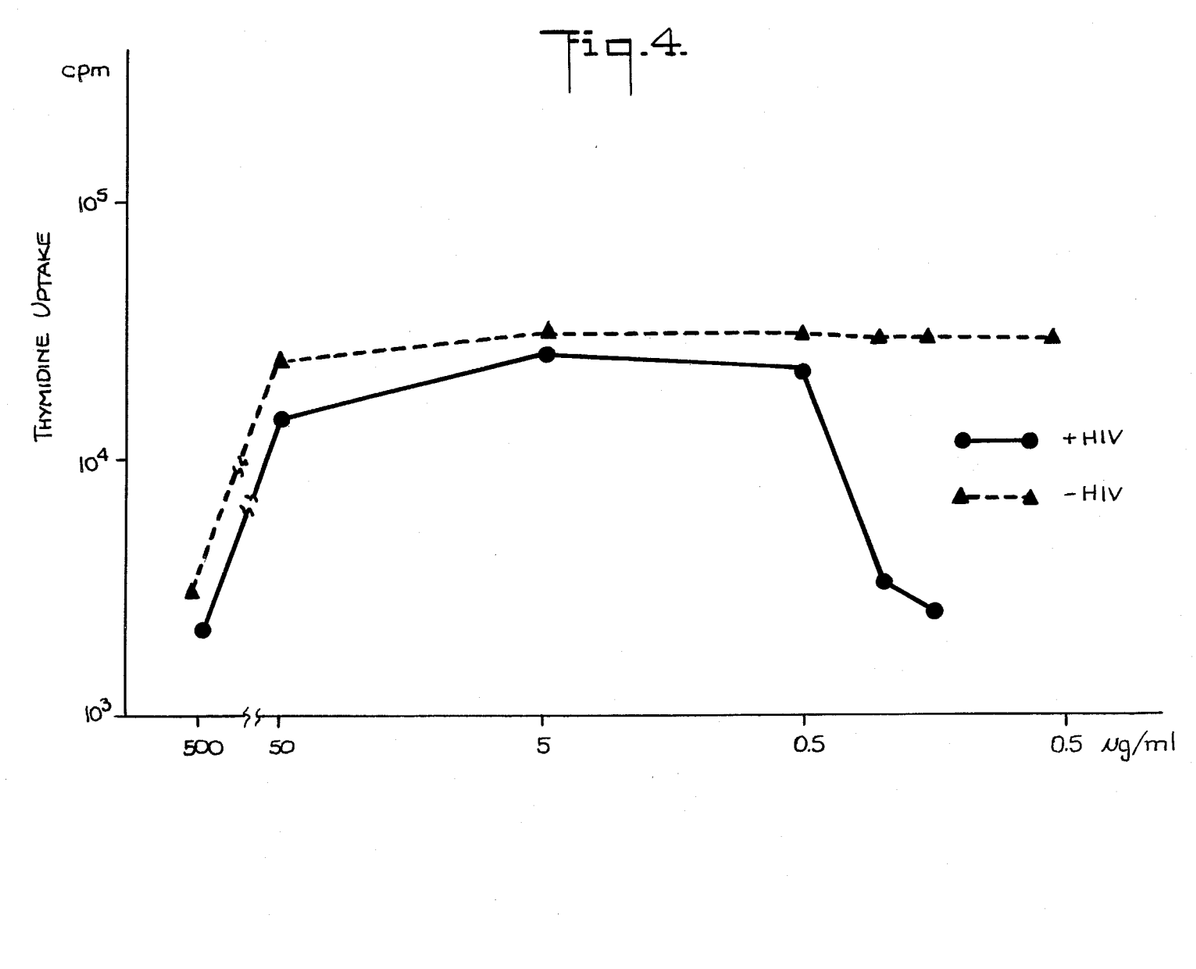
FIG. 4 shows results of in vitro viability studies when 3'-fluoro-2',-3'-dideoxyguanosine was added to HIV infected cells.

In analogy to this FIG. 4 shows the in vitro antiviral activity of 3'-fluoro-2',3'-dideoxyguanosine. The realization and interpretation was done according to the explanation for FIG. 2. This active material at a concentration of less than 1.5$\mu g./ml.$ protects the cells already with half maximal action against the pathogenic effect of the 1:40 dilution of HIV patent liquid.

Figure 5:
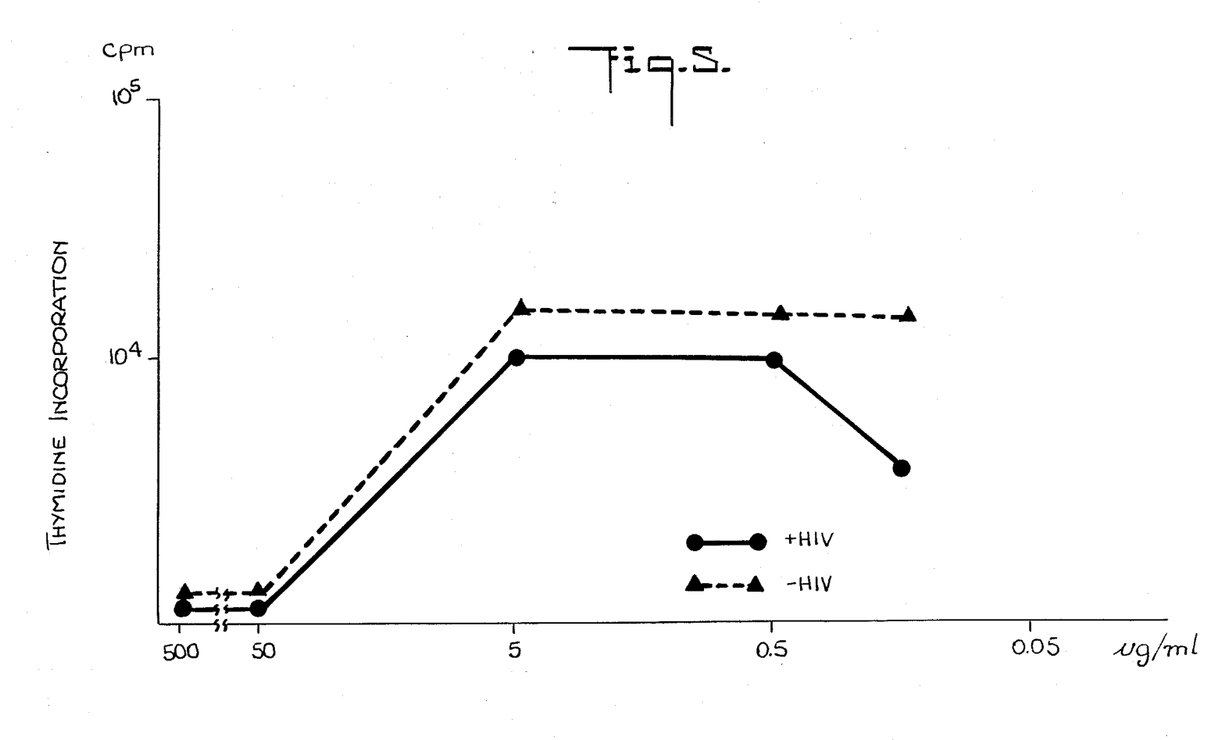
FIG. 5 shows results of in vitro viability studies when 3'-azido-2',-3'-dideoxyinosine was added to HIV infected cells.

In FIG. 5, experiments are presented in which 3'-azido-2',3'-dideoxyinosine was the drug administered. Toxicity of the inosine compound was higher, but again the rate of thymidine incorporation increased in the HIV infected cell line, and nearly equalled that of non-infected $T_4$ cell lines.

EXAMPLE I

In the following experiment, the suppression of HIV production in phytohemagglutinin (PHA) stimulated peripheral blood lymphocytes were studied.

Samples of peripheral blood lymphocytes were stimulated with PHA, and this was followed by addition of HIV virus directly to the culture flasks in which the cells were grown. In those sample runs in which drug was added, this followed immediately after the introduction of the virus to the culture flask.

The amount of HIV present following administration of the drug was determined by radioimmunoassay for the component of HIV known as "p24". The radioimmunoassay used has a sensitivity of 20–0.625 $\mu g/ml$ tested.

It was essential when running this test to determine the viability of the PBLS as well. This was done via incorporation of radioactive thymidine, as set forth in Example I, supra.

Different concentrations of each drug were used: for azido-thymidine (AZT), these were 1, 0.1, and 0.01 $\mu M$, while for 3'-azido-2',3'-dideoxy guanosine (ADG), the doses were 3, 0.3, 0.003, and 0.0003 $\mu g$. Positive controls ("+"), received HIV, but no drug, while negative controls ("−"), received drug, but no virus. Assays were run at 4, 7, 11, and 14 days of culture. At each point, the culture medium was replaced by fresh medium.

These results are set out in Table 1:

TABLE 1

| Pt/Sample | Day | Date | Counts 1 | Counts 2 | Av. | Net | % B/Bo | ng p24/ml |
|---|---|---|---|---|---|---|---|---|
| Total Counts | | | 5639 | 5478 | 5423.5 | | | |
| Blank | | | 151 | 138 | 144.5 | 0.0 | | |
| "O" Standard | | | 3187 | 2932 | 3059.5 | 2915.0 | 100.0% | |
| 0.625 ng | | | 2695 | 2724 | 2709.5 | 2565.0 | 88.0% | |
| 1.25 ng | | | 2492 | 2497 | 2494.5 | 2350.0 | 80.6% | |
| 2.5 ng | | | 1981 | 2105 | 2043 | 1898.5 | 65.1% | |
| 5.0 ng | | | 1494 | 1472 | 1483 | 1338.5 | 45.9% | |
| 10.0 ng | | | 815 | 899 | 857 | 712.5 | 24.4% | |
| 20.0 ng | | | 546 | 498 | 522 | 377.5 | 13.0% | |
| AZT 1 | 4 | | 1700 | 1684 | 6692 | 1547.5 | 53.1% | 3.7 |
| AZT 0.1 | 4 | | 1600 | 1708 | 1689 | 1544.5 | 53.0% | 3.7 |
| AZT 0.01 | 4 | | 1759 | 1692 | 1725.5 | 1581.0 | 54.2% | 3.6 |
| + | 4 | | 307 | 314 | 310.5 | 166.0 | 5.7% | 20 |
| + | 4 | | 3209 | 3165 | 3187 | 3042.5 | 104.4% | 0 |
| − | 4 | | 2709 | 2771 | 2740 | 2595.5 | 89.0% | 0 |
| ADG 3 | 4 | | 1587 | 1730 | 1658.5 | 1514.0 | 51.9% | 3.8 |
| ADG 0.3 | 4 | | 1215 | 1208 | 1211.5 | 1067.0 | 36.6% | 6.8 |
| ADG 0.03 | 4 | | 357 | 360 | 358.5 | 214.0 | 7.3% | 20 |
| ADG 0.003 | 4 | | 396 | 376 | 386 | 241.5 | 8.3% | 20 |
| AZT 1 | 7 | | 2310 | 1957 | 2133.5 | 1989.0 | 68.2% | 2.2 |
| AZT 0.1 | 7 | | 2304 | 2369 | 2336.5 | 2192.0 | 75.2% | 1.6 |

TABLE 1-continued

| Pt/Sample | Day | Date | Counts 1 | Counts 2 | Av. | Net | % B/Bo | ng p24/ml |
|---|---|---|---|---|---|---|---|---|
| AZT 0.01 | 7 | | 1959 | 1960 | 1959.5 | 1815.0 | 62.3% | 2.7 |
| + | 7 | | 224 | 232 | 228 | 83.5 | 2.9% | 20 |
| + | 7 | | 293 | 239 | 266 | 121.5 | 4.2% | 20 |
| − | 7 | | 2649 | 2839 | 2744 | 2599.5 | 89.2% | 0 |
| ADG 3 | 7 | | | 2255 | 2255 | 2110.5 | 72.4% | 1.8 |
| ADG 0.3 | 7 | | 1047 | 843 | 945 | 800.5 | 27.5% | 10 |
| ADG 0.03 | 7 | | 316 | 262 | 289 | 144.5 | 5.0% | 20 |
| ADG 0.003 | 7 | | 294 | 283 | 288.5 | 144.0 | 4.9% | 20 |
| AZT 1 | 11 | | 2458 | 2483 | 2470.5 | 2326.0 | 79.8% | 1.25 |
| AZT 0.1 | 11 | | 2531 | 2340 | 2435.5 | 2291.0 | 78.6% | 1.3 |
| AZT 0.01 | 11 | | 501 | 485 | 493 | 348.5 | 12.0% | 20 |
| + | 11 | | 249 | 236 | 242.5 | 98.0 | 3.4% | 20 |
| + | 11 | | 242 | 260 | 251 | 106.5 | 3.7% | 20 |
| − | 11 | | 2770 | 2817 | 2793.5 | 2649.0 | 90.9% | 0 |
| ADG 3 | 11 | | 2653 | 2592 | 2622.5 | 2478.0 | 85.0% | 0.9 |
| ADG 0.3 | 11 | | 277 | 287 | 282 | 137.5 | 4.7% | 20 |
| ADG 0.03 | 11 | | 225 | 242 | 233.5 | 89.0 | 3.1% | 20 |
| ADG 0.003 | 11 | | 201 | 225 | 213 | 68.5 | 2.3% | 20 |
| AZT 1 | 14 | | 2652 | 2558 | 2605 | 2460.5 | 84.4% | 0.94 |
| AZT 0.1 | 14 | | 2151 | 2048 | 2099.5 | 1955.0 | 67.1% | 2.3 |
| AZT 0.01 | 14 | | 351 | 299 | 325 | 180.5 | 6.2% | 20 |
| + | 14 | | 277 | 309 | 293 | 148.5 | 5.1% | 20 |
| + | 14 | | 227 | 245 | 236 | 91.5 | 3.1% | 20 |
| − | 14 | | 2393 | 2665 | 2529 | 2384.5 | 81.8% | 1.1 |
| ADG 3 | 14 | | 2725 | 2721 | 2723 | 2578.5 | 88.5% | 0.6 |
| ADG 0.3 | 14 | | 316 | 297 | 306.5 | 162.0 | 5.6% | 20 |
| ADG 0.03 | 14 | | 292 | 282 | 287 | 142.5 | 4.9% | 20 |
| ADG 0.003 | 14 | | 288 | 260 | 274 | 129.5 | 4.4% | 20 |

It is interesting to note that ADG, at a concentration of 3 μg, was slightly more effective than AZT. Both AZT and ADG began to lose efficacy at their lowest concentrations at about the same time. The drugs do not show toxicity against the PBL either, as the "counts" resulting from thymidine indicate that cell viability remained good.

Table 2 presents this data in term of a RIA adjusted for $10^6$ cells/ml.

TABLE 2

| Pt/Sample | Day | NET Cnts | CPM/ml | CELL + 06 | CPM/1 + 06 CELLS |
|---|---|---|---|---|---|
| AZT 1 UM | 7 | 380.0 | 2.9 E + 03 | 3.72 | 7.66 E + 02 |
| AZT 0.1 UM | 7 | 47.0 | 3.5 E + 02 | 4.08 | 8.64 E + 01 |
| AZT 0.01 UM | 7 | 784.0 | 5.9 E + 03 | 3.3 | 1.78 E + 03 |
| +CONTROL | 7 | 41,186.0 | 3.1 E + 05 | 2.92 | 1.06 E + 05 |
| +CONTROL | 7 | 62,298.0 | 4.7 E + 05 | 3.68 | 1.27 E + 05 |
| −CONTROL | 7 | 21.0 | 1.6 E + 02 | 4 | 3.94 E + 01 |
| ADG 3 UG | 7 | 325.0 | 2.4 E + 03 | 3.7 | 6.59 E + 02 |
| ADG 0.3 UG | 7 | 1,704.0 | 1.3 E + 04 | 3.92 | 3.26 E + 03 |
| ADG 0.03 UG | 7 | 36,160.0 | 2.7 E + 05 | 2.68 | 1.01 E + 05 |
| ADG 0.003 UG | 7 | 43,236.0 | 3.2 E + 05 | 3.78 | 8.58 E + 04 |
| AZT 1 UM | 11 | (1,084.0) | −8.1 E + 03 | 5.02 | −1.62 E + 03 |
| AZT 0.1 UM | 11 | 163.0 | 1.2 E + 03 | 4.9 | 2.49 E + 02 |
| AZT 0.01 UM | 11 | 3,681.0 | 2.8 E + 04 | 3.84 | 7.19 E + 03 |
| +CONTROL | 11 | 44,567.0 | 3.3 E + 05 | 4.22 | 7.92 E + 04 |
| +CONTROL | 11 | 48,778.0 | 3.7 E + 05 | 4.44 | 8.24 E + 04 |
| −CONTROL | 11 | (1,225.0) | −9.2 E + 03 | 5.72 | −1.61 E + 03 |
| ADG 3 UG | 11 | (1,280.0) | −9.6 E + 03 | 5.84 | −1.64 E + 03 |
| ADG 0.3 UG | 11 | 24,287.0 | 1.8 E + 05 | 4.84 | 3.76 E + 04 |
| ADG 0.03 UG | 11 | 52,529.0 | 3.9 E + 05 | 4.48 | 8.79 E + 04 |
| ADG 0.003 UG | 11 | 38,738.0 | 2.9 E + 05 | 4.7 | 6.18 E + 04 |
| AZT 1 UM | 14 | 76.0 | 5.7 E + 02 | 3.68 | 1.55 E + 02 |
| AZT 0.1 UM | 14 | 519.0 | 3.9 E + 03 | 3.98 | 9.78 E + 02 |
| AZT 0.01 UM | 14 | 18,411.0 | 1.4 E + 05 | 5.74 | 2.41 E + 04 |
| +CONTROL | 14 | 15,864.0 | 1.2 E + 05 | 5.02 | 2.37 E + 04 |
| +CONTROL | 14 | 27,525.0 | 2.1 E + 05 | 4.72 | 4.37 E + 04 |
| −CONTROL | 14 | (405.0) | −3.0 E + 03 | 3.98 | −7.63 E + 02 |
| ADG 3 UG | 14 | (12.0) | −9.0 E + 01 | 3.5 | −2.57 E + 01 |
| ADG 0.3 UG | 14 | 19,307.0 | 1.4 E + 05 | 3.08 | 4.70 E + 04 |
| ADG 0.03 UG | 14 | 30,818.0 | 2.3 E + 05 | 3.66 | 6.32 E + 04 |
| ADG 0.003 UG | 14 | 31,978.0 | 2.5 E + 05 | 4.36 | 5.67 E + 04 |

These results show that ADG is effective in doses of from 0.3 to 3 μg/ml. One would expect similar results for 3'-azido-2,-3'-dideoxyinosine.

EXAMPLE II

The Experiment as described in Example II was repeated for 3'-fluoro-2'-3'-dideoxyguanosine. 3'-fluoro-2'-3'-dideoxyguanosine was synthesized in analogy to the synthesis of 3'-azido-2',3'-dideoxyguanosine (Imazawa and Eckstein, J. Org. Chem. 43: 3044) (1978) by transglycosidation of 3'-fluoro-3'-deoxythymidine (synthesized according t G. Etzold et al., Tetrahedron 27:2463) (1971) with palmitoyl guanine in acetonitrile under reflux for 60 minutes with bis(trimethylsilyl)-acetamide and trimethylsilyl trifluoromethanesulfonate.

Chromatography on Kieselgel yields a product which on TLC (CHCl$_3$/MeOH, 9:1) has a slightly larger R$_F$ (0.43) than thymine (0.38). It is reacted at 50° C. overnight in MeOH saturated with NH$_3$ After evaporation to dryness the residue is dissolved in H$_2$O/MeOH and chromatographed on a LiChroprep RP-18 column with 50 mM triethylammonium bicarbonate (pH 7.5) containing 6% acetonitrile. After evaporation of the product-containing fractions and reevaporation with MeOH a crystalline residue of 9-(3-fluoro-2,3-dideoxy-β-D-ribofuranoyl)guanine is obtained; mP>230°, $^1$H-NMR (DMSO), δ, 6.15 ppm (dd, 1H, J$_{3,H,F}$=53 Hz, H=3'), 4.14 (dm, 1H, J$_{4,H,3'F}$=32 Hz, H-4'). HPLC on ODS-Hypersil with a linear gradient of 100 mM triethylammonium bicarbonate (pH 7.5) and acetonitrile (0–15% in 15 minutes), retention times: 8.8 min for the β-anomer, 6.8 min for the α-anomer. Yield Approx. 15%.

The pharmaceutical compositions according to the present invention can contain the active material in free form or in the form of physiologically acceptable salts, namely in the form of a compound or a mixture of compounds of the above given general formula. In addition, the pharmaceutical composition can contain pharmaceutical additives and diluents usual for the intended form of administration.

Administration can be oral, parenteral, intrathecal, or intravenous, with oral administration being preferred. Preferred dosages range from about 1 to about 20g per day per 70 kilograms of body weight when administered to a human subject. Optimum dosage and mode of administration will vary from subject to subject.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

We claim:

1. Composition useful in treating an infection of human immunodeficiency virus comprising an anti human immunodeficiency virus effective amount of 3'-azido-2',3'-dideoxyinosine.
2. Composition according to claim 1, wherein said compound is present in an amount from about 1 to about 20 g per daily dosage.
3. Method of claim 1, wherein said compound is 3,'-azido-2',3,'-dideoxyguanosine.
4. Method of claim 1, wherein said compound is 3,'-fluoro-3'-deoxythymidin.
5. Method of claim 1, wherein said compound is 3,'-fluoro-2',3,'-dideoxyguanosine.
6. Method of claim 1, wherein said compound is 3,'-azido-2,'3'-dideoxyinosine.
7. Method of claim 1, wherein said compound is administered orally, parenterally, intrathecally, or intravenously.
8. Method of claim 1, wherein said compound is administered orally.
9. Method of claim 1, wherein said compound is administered in an amount from about 1 g to about 10 g/day per 70 kg of body weight.
10. Method for treating a human infected by human immunodeficiency virus comprising administering to said infected human an anti-human immunodeficiency virus effective amount, of a compound,, selected from the group consisting of 3'-azido-2',3'-dideoxyguanosine, 3'-fluoro-3'-deoxythymidine, 3,'-fluoro-2',3'-dideoxyguanosine and 3'-azido-2',3'-dideoxyinosine.
11. Method for protecting cells against HIV pathogenesis comprising administering to a human with HIV pathogenesis an amount of ,a compound selected from the group consisting of 3'-azido-2,3'-dideoxyguanosine, 3'-fluoro-3'deoxythymidine, 3'-fluoro-2',3'-dideoxyguanosine and 3'-azido-2',3'-dideoxyinosine effective to protect cells of said human against HIV pathogenesis.
12. 3,'-azido-2',3'-dideoxyinosine.

* * * * *